United States Patent [19]

Spector

[11] 4,026,879

[45] May 31, 1977

[54] ANTIGEN-CONTAINING PROPRANOLOL DERIVATIVES

[75] Inventor: Sidney Spector, Livingston, N.J.

[73] Assignee: Hoffmann-La Roche Inc., Nutley, N.J.

[22] Filed: Mar. 23, 1976

[21] Appl. No.: 669,784

[52] U.S. Cl. .............................. 260/121; 23/230 B; 260/78 A; 260/112 R; 260/112 B; 424/1; 424/12; 424/85; 424/88
[51] Int. Cl.$^2$ ........................................ C07G 7/00
[58] Field of Search ...... 424/12; 260/112 R, 112 B, 260/121, 78 A

[56] References Cited

UNITED STATES PATENTS

| | | | |
|---|---|---|---|
| 3,690,834 | 9/1972 | Goldstein et al. | 23/230 |
| 3,704,282 | 11/1972 | Spector | 260/112 R X |
| 3,852,157 | 12/1974 | Rubenstein et al. | 424/12 X |
| 3,878,187 | 4/1975 | Schneider et al. | 260/121 |
| 3,975,342 | 8/1976 | Gross | 260/121 X |
| 3,988,430 | 10/1976 | Dixon et al. | 260/112 R X |

*Primary Examiner*—Howard E. Schain
*Attorney, Agent, or Firm*—Samuel L. Welt; George M. Gould

[57] ABSTRACT

New hapten compositions useful in preparing antigens which may be employed in eliciting antibodies useful in immunoassay, particularly radioimmunoassay for propranolol. Utilizing an enantiomer in formation of the hapten allows preparation of an antibody which is able to discriminate between enantiomers selectively.

4 Claims, No Drawings

ANTIGEN-CONTAINING PROPRANOLOL DERIVATIVES

BACKGROUND OF THE INVENTION

A radioimmunoassay for catecholamines is described in U.S. Pat. No. 3,704,282. The antigen utilized for eliciting the needed catecholamine specific antibody was prepared by directly coupling the catecholamine to the protein or polypeptide immunogenic carrier using a carbodiimide coupling agent. The resulting antigen is formed by an amide bond linkage of the amine group of the catecholamine with pendant carboxy groups of the support materials.

Faraj et al. in a paper appearing in Pharmacologist, June 1974, decribe the preparation of an antibody specific to tyramine. The antigen used for eliciting this antibody is prepared by coupling p-aminohippuric acid to methylated bovine serum albumin followed by diazotization of the amino group and reaction of the diazonium intermediate with tyramine.

U.S. Pat. No. 3,690,834 teaches the preparation of antigens and antibodies to a large number of biologically active compounds. The antigens are prepared by linking the compounds to a protein carrier through a suitable linkage. These antigens may then be used to elicit antibodies by conventional procedures. The antibodies and spin-labeled derivatives of the biologically active compounds are then used in an assay procedure.

DESCRIPTION OF THE INVENTION

The present invention relates to an immunoassay for detection of the valuable therapeutic agent propranolol. This compound has the formula

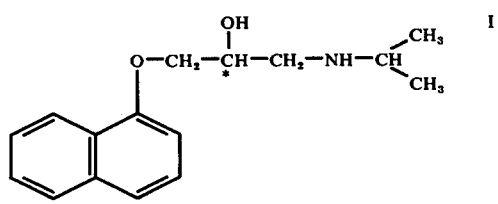

It is evident that propranolol has an asymmetric carbon atom (*) and thus the compound has two optical enantiomers. Only the l-form has pharmacological activity as a beta adrenergic blocking agent which provides its therapeutic utility in the treatment of cardiac arrythmias and hypertension. It is thus desirable to provide an immunoassay which can differentiate the l-form and the d-form of propranolol and determine l-propranolol in the presence of the d-isomer. Previously available methods for determination of propranolol in biological fluids are not only laborious but cannot differentiate the l-form from the d-form of this compound. wherein $n$ is an integer from 2 to 6;

Since propranolol is not antigenic per se it is necessary to utilize haptenic compounds of the formula

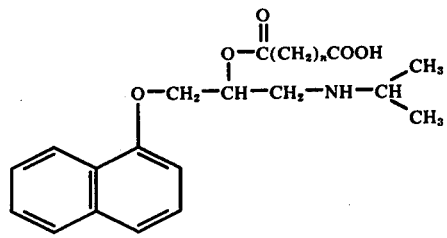

wherein $n$ is an integer from 2 to 6;
as a means of preparing propranolol containing antigens. The aforesaid haptens are readily obtained by reacting propranolol with a dibasic carboxylic acid of the formula

$$HOOC-(CH_2)_n-COOH \quad \text{III}$$

where $n$ is as above
or a derivative thereof selected from the mono-acid-halides and anhydrides utilizing conditions well known in the art for ester bond formation.

A particularly preferred hapten is propranolol hemisuccinate prepared by reaction of propranolol or a mineral acid addition salt thereof, i.e., the hydrochloride with succinic anhydride preferably in the presence of an organic base such as pyridine at elevated temperatures.

In order to prepare the antigens needed in the present invention, it is necessary that the hapten of formula II be covalently bonded through the carboxylic group to a conventional immunogenic carrier material. As used herein, the term "immunogenic carrier material" is meant to include those materials which have the property of independently eliciting an immunogenic response in a host animal and which can be covalently coupled to the above described haptens. Suitable carrier materials include, for example, proteins; natural or synthetic polymeric compounds such as polypeptides, e.g., polylysine or copolymers of other amino acids; polysaccharides, and the like. Particularly preferred carrier materials are proteins and polypeptides, especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin, and bovine gamma globulin. Other protein products will be suggested to one skilled in the art. It is generally preferred but not necessary that proteins be utilized which are foreign to the animal hosts in which the resulting antigen will be employed.

The covalent coupling of the hapten to the immunogenic carrier material can be carried out in a manner well known in the art for establishing amide bonds. One type of method for coupling does not require the isolation of activated intermediates. Such methods include the mixed anhydride method or the use of EEDQ (N-ethoxy-carbonyl-2-ethoxy-1,2-dihydroquinoline) as coupling agent.

Alternatively, it is possible to utilize methods involving the isolation of an activated form of the hapten prior to coupling. An example of such method involves formation and isolation of the N-hydroxy-succinimide ester.

A preferred method of coupling involves activating the carboxyl group of the hapten without isolation of an intermediate utilizing the mixed anhydride obtained by reaction with isobutylchloroformate. The hapten is dissolved in an anhydrous, water-miscible organic solvent, usually dioxane, and the solution is neutralized with an equimolar quantity of triethylamine. After stirring at room temperature the temperature of the mixture is reduced to between 0° and 8° C. An equimolar quantity plus 10% excess of isobutylchloroformate is then added and stirring is continued. Meanwhile, the carrier protein, e.g., bovine serum alumin, is dissolved in water and the pH is adjusted to 9.0 with NaOH. The quantity of carrier used in equivalent to the molar quantity of hapten divided by the theoretical number of reactive groups on the carrier. Organic solvent is added to the carrier solution and the solution is cooled to between 0° and 8° C. The solution is then added to the activated hapten and coupling is allowed to proceed for 30 minutes to overnight. The final ratio of organic solvent to water is 1:1. The mixture is then adjusted to neutrality and aqueous solution is effected.

The antigens of the present invention may be utilized to induce formation of antibodies specific to propranolol or an enantiomer thereof in host animals by injecting the antigen in such a host, preferably using a conventional adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with propranolol, an enantiomer of propranolol or an antigen prepared therefrom, as described above.

The specific antibodies of the present invention are useful as reagents for the determination of propranolol or enantiomers thereof. In such an assay, a known amount of labeled propranolol is mixed with the above antibody and a sample containing some propranolol is added. The amount of propranolol in the sample can be determined by measuring the inhibition of the binding to the specific antibodies of the labeled propranolol by the unknown sample. The reagents may be added in any order. A suitable assay procedure for this purpose is described in greater detail in U.S. Pat. No. 3,709,868.

Suitable labeled propranolol derivatives for assay purposes include radioisotopically labeled propranolol or an enantiomer thereof, particularly, those labeled with tritium ($^3H$), carbon 14 ($^{14}C$) or with iodine 125 ($^{125}I$). One may also employ propranolol labeled with any other unique and detectable label such as, for example, an electron spin resonance group. Examples of the use of various electron spin resonance labelled molecules in bioassays are to be found in U.S. Pat. Nos. 3,453,288; 3,481,952 and 3,507,876. Other suitable labels include chromophores, fluorophors, enzymes, red blood cells, latex particles, etc.

In a preferred embodiment of the present invention antisera against propranolol was produced in rabbits immunized with propranolol conjugated to bovine serum albumin through a hemisuccinate linking group. The antiserum against d,1-propranolol recognized both d- and 1-propranolol enantiomers to the same degree. However, antiserum produced form an antigen using 1-propranolol as hapten was able to discriminate the 1-propranolol selectively.

The antisera were used to develop radioimmunoassays for d,1-propranolol and 1-propranolol. Such assays can detect as little as 10 pg. of the test substances. Moreover, it was discovered that metabolites of propranolol do not interfere with the assay unless concentrations are very high.

The assay of the present invention was utilized to determine the serum and heart levels of d- and 1-propranolol in the rat following i.v. injection of 1 mg/kg of racemic propranolol declines rapidly in the blood following the injection. Concomitantly, there is a rapid accumulation of 1-propranolol by the heart. The d-enantiomer remains in the blood and is metabolized rapidly. Thus, the instant assay established stereospecific uptake of 1-propranolol by the rat heart, and a more rapid metabolism of the d-form.

EXAMPLE 1

Preparation of Immunogen

Propranolol was conjugated to bovine serum albumin (BSA) by initially making a propranolol hemisuccinate and then forming an amide linkage between the amine groups of BSA and the carboxy group of the propranolol hemisuccinate.

Hemisuccinate formation: 500 mg. (1.7 mM) of d,1-propranolol hydrochloride and 170 mg. (1.7 mM) of succinic anhydride were dissolved in 3 ml. of pyridine in a 15 ml. capped test tube. The test tube was heated at 70° C. for 5 hours, then 3 ml. of water were added. The pH of the solution was adjusted to 3.0 with 1N CH1 and extracted with 10 ml. of diethyl ether. The organic layer was washed twice with water and evaporated to dryness under vacuum.

The d,1-propranolol hemisuccinate was conjugated to BSA by the mixed anhydride technique using the isobutylchloroformate and triethylamine method of Erlanger et al., J. Biol. Chem. 234; 1090 (1959).

A total of 38 mg. of d,1-propranolol hemisuccinate was dissolved in 2 ml. of dry dioxane and 0.05 mM of triethylamine (1:10 dilution in dry dioxane — 0.07 ml.) were added. The solution was stirred and cooled to 8° C. in an ice water bath. A total of 0.05 mM of isobutyl chloroformate 1:10 dilution in dry dioxane in 0.065 ml.) were added to the cooled mixture. After stirring, the solution was allowed to sit at 8° C. for 20–30 minutes with occasional shaking.

A total of 50 mg. of crystalline bovine serum albumin was dissolved in 10 ml. of distilled water. The solution was adjusted to pH 7, then 8 ml. of dioxane were added slowly. The pH was then adjusted to 9 utilizing 0.05 M sodium hydroxide. The solution was kept at 8° C. during this entire procedure.

The solution containing the d,1-propranol hemisuccinate anhydride was added dropwise to the bovine serum albumin solution with constant stirring at 8° C. The pH was maintained between 8.5 and 9.5 by the addition of a few drops of sodium hydroxide. The reaction was considered complete when the pH did not drop on the addition of the anhydride solution. The reaction mixture was then allowed to stand at 8° C. for an additional 20–30 minutes. The resulting solution may be utilized to elicit antibody formation after adjustment of the protein content by dilution to 1 mg/ml.

L-propranolol immunogen was synthesized using the same method as described above.

EXAMPLE 2

Immunization

New Zealand albino rabbits were immunized with propranolol-BSA immunogens once a week for 4 weeks and then once every 2 to 4 weeks. The immunogen was dissolved in phosphate-buffered saline (pH 7.4) and emulsified with an equal amount of complete Freund's adjuvant. One ml. of emulsion containing 500 µg of immunogen was injected into four foot pads and intramuscularly into both thighs. Bleedings were taken from the central ear artery 6 to 8 days after the third booster injection. Blood was allowed to clot overnight at 4° C. and centrifuged at 2,000 rpm for 15 minutes to separate serum.

EXAMPLE 3

Titration of Antibodies in Antisera

Antisera were diluted in a 2.5% solution of normal rabbit serum in 1:10 phosphate buffered saline. 0.4 ml. of this mixture was added to the assay tubes (10 × 75 mm). 10 µl. of unknown or standard solutions were added to the tubes. 0.1 ml. of radioactive d,1-propranolol solution containing 60 pg. (approximately 2,500 cmp) for antiserum against d,1-propranolol and 120 pg. (approximately 5,000 cpm) for antiserum against 1-propranolol was subsequently added. The tubes were incubated overnight at 4° C. Antibody bound propranolol was separated by the addition of 0.5 ml. of saturated ammonium sulfate. The pellet was washed once with 0.8 ml. of 50% saturated ammonium sulfate, then dissolved in 0.5 ml. of water and transferred into a counting vial. The tube was washed twice with 3 ml. of Riafluor. Another portion of 6 ml. Riafluor was added to the vial to give a total volume of 12 ml., and the radioactivity was counted in a scintillation counter. The dilutions of the antisera used were 1:10,000 and 1:1000 respectively against d,1-propranolol and 1-propranolol.

EXAMPLE 4

Procedure in Animals

Pharmacokinetics of 1- and d-propranolol was followed in a group of rats weighing 230 g. ± 2 g. (S.E). One mg/kg of d,1-propranolol was injected intravenously through the tail vein. AT varying times, groups of three rats were killed; blood and the heart taken from each animal. Serum was separated by centrifugation and kept frozen until assayed. Amounts of d,1-proporanolol and 1-propranolol in serum were determined by radioimmunoassay with the use of specific antisera. Because of the high sensitivity of the assay, an aliquot of 10 or 20 µl of unknown samples in the proper dilution was used for the assay. Hearts were homogenized in 0.01 N HCl and centrifuged at 1000 xg. for 15 min. The supernatant was kept frozen until assayed. Recovery was determined by homogenizing hearts in the presence of a known amount of d,1-propranolol and then going through the entire procedure. Recovery values were 99 ± 2%. Rats weighing 250–240 g. were anesthetized with Nembutal 50 mg/kg i.p. Heart rate and blood pressure were recorded from femoral artery by means of pressure transducer. Drugs were administered through a cannula attached to femoral vein. One mg/kg of d,1-propranolol was administered intravenously. At varying time, 0.5 µg/kg of isoproterenol was injected. The inhibition by propranolol of heart rate increase caused by isoproterenol was calculated.

EXAMPLE 5

Sensitivity and Specificity of Radioimmunoassay

The sensitivity of radioimmunoassay for d,1-propranolol and its 1-isomer in phosphate-buffered saline and serum were determined. As little as 10 pg. of propranolol can be detected with both antisera and the assay is linear up to 5,000 pg. for d,1-propranolol and 2,000 pg. for 1-propranolol. Identical standard curves were obtained with phosphate-buffered saline and serum indicating that there are no interfering substances in serum.

The specificity of both antisera are shown in Table 1 below:

TABLE 1

| COMPOUND | STRUCTURE | $ID_{50}$ AND 95% CONFIDENCE LIMITS | |
|---|---|---|---|
| | | ANTI-d,1-PROPRANOLOL | ANTI-1-PROPRANOLOL |
| 1-PROPRANOLOL | $R_1$=CH$_2$—CH—CH$_2$NHCH(CH$_3$)$_2$, OH; $R_2$=—H | 321 pg (313–330) | 120 pg (112–129) |
| d-PROPRANOLOL | | 314 pg (307–322) | 1656 pg (1572–1745) |
| PROPRANOLOL GLYCOL | $R_1$=CH$_2$—CH(OH)—CH$_2$—OH; $R_2$=H | 4393 pg (4206–4579) | 1113 pg (1055–1172) |

TABLE 1-continued

COMPETITION WITH ³H-PROPRANOLOL FOR BINDING SITE

Structure header (common naphthol structure): O—$R_1$ on naphthalene, $R_2$ at 4-position.

| COMPOUND | STRUCTURE | ID$_{50}$ AND 95% CONFIDENCE LIMITS | |
|---|---|---|---|
| | | ANTI-d,l-PROPRANOLOL | ANTI-l-PROPRANOLOL |
| 4-HYDROXY-PROPRANOLOL | $R_1$=$CH_2$—CH(OH)—$CH_2$NHCH($CH_3$)$_2$; $R_2$=—OH | 21,688 pg (21,010–22,386) | 4072 pg (3860–4288) |
| 1-NAPHTHOL | $R_1$=—H; $R_2$=—H | 25% AT 100 ng | 45% AT 100 ng |
| 1-NAPHTHOXY ACETIC ACID | $R_1$=—$CH_2$COOH; $R_2$=H | 10% AT 100 ng | 25% AT 100 ng |
| 1,4-NAPHTHALENE-DIOL | $R_1$=H; $R_2$=—OH | NO INHIBITION AT 100 ng | 17% AT 100 ng |
| ISOPROPYLAMINE | $H_2N$—CH($CH_3$)$_2$ | | NO INHIBITION AT 100 ng |
| PRONETHALOL | naphthalen-2-yl—CH(OH)—$CH_2$NHCH($CH_3$)$_2$ | 45% AT 100 ng | 29.5 ng (28–31) |
| DICHLOROISOPROTERENOL | 3,4-dichlorophenyl—CH(OH)—$CH_2$—NH—CH($CH_3$)$_2$ | 13% AT 100 ng | NO INHIBITION AT 100 ng |
| ISOPROTERENOL | 3,4-dihydroxyphenyl—CH(OH)—$CH_2$—NH—CH($CH_3$)$_2$ | | NO INHIBITION AT 100 ng |
| EPINEPHRINE | 3,4-dihydroxyphenyl—CH(OH)—$CH_2$—NH—$CH_3$ | | NO INHIBITION AT 100 ng |
| NOREPINEPHRINE | 3,4-dihydroxyphenyl—CH(OH)—$CH_2$—$NH_2$ | | NO INHIBITION AT 100 ng |
| DOPAMIN | 3,4-dihydroxyphenyl—$CH_2$—$CH_2$—$NH_2$ | | NO INHIBITION AT 100 ng |

ID$_{50}$ refers to the amount of compound required to produce 50% inhibition of ³H-propranolol-antibody complex formation. Although antiserum against d,l-propranolol recognized both d- and l-propranolol to the same degree, antiserum against l-propranolol bound l-propranolol more selectively than the d-isomer. With antiserum against l-propranolol, ID$_{50}$ for d-propranolol was 14 times that for the l-isomer. ID$_{50}$ values for 1-(1-naphthoxy)-2,3-propylene glycol, the most cross-reactive metabolite of propranolol tested, were 9-14 times the values for l-propranolol and d,l-propranolol. 4-Hydroxy-propranolol, one of the major metabolites of propranolol possessing beta-adrenergic blocking activity was not recognized by the l-antibody unless concenrations were 35 times greater or by the d,l-antibody unless concentrations were 70 times greater. Other metabolites, such as 1-naphthol, 1-naphthoxy acetic acid, 1,4-naphthalene-diol and isopropylamine did not interfere with the assay unless concentrations were at least 1,000 times greater. Pronethalol and dichloroisoproterenol, other beta-adrenergic blocking agents, were not significant recognized by either antisera. There was no cross-reaction between both antisera and biogenic amines and isoproterenol.

EXAMPLE 6

Disposition of Propranolol in Rats

Table 2 shows the results obtained for blood-levels using the two different antibodies. From those results the level of d- and l-propranolol was calculated. These calculations correct for the fact that the l-antibody can bind a small fraction of the d-form. (100 pg. of the d isomer will be recognized by the antibody as though it were 7 pg of the l-form). Both isomers show a biphasic decay curve, with a rapid initial decline during the first 15–20 minutes, followed by a second slower decline. Initially, the level of d-propranolol is three times higher than that of l-propranol. The d-propranolol disappears much faster, with a half-life of 23.8 minutes (correlation factor 0.9987) while the half-life for l-propranolol is almost twice that of the d-isomer-52.0 minutes (correlation factor of 0.9958). Most of the propranolol found in the heart up to 90 minutes was l-form (882 ± 5%). However, after 2 hours post injection, only l-propranolol could be found in the heart.

After half an hour, the decline of l-propranolol in the heart was almost parallel to that found in the blood-half life of 62 minutes (correlation factor .998). Increase in heart rate in response to isoproterenol 0.5 g/kg i.v. was compared before and at varying time after the administration of propranolol. The increase in heart rate due to isoproterenol was markedly suppressed by propranolol for the first 30 minutes after the administration of 1 mg/kg i.v. The effect of propranolol on heart rate disappeared by 90 minutes after its administration.

I claim:

1. An antigen consisting essentially of a propranolol hapten of the formula

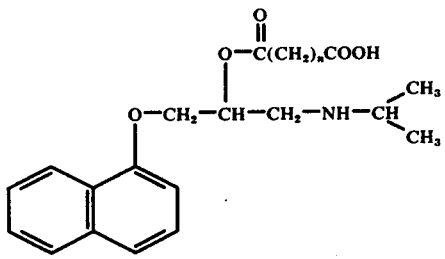

wherein $n$ is an integer from 2 to 6;
said hapten being convalently bonded to an immunogenic carrier material through the carboxyl group.

2. The antigen of claim 1 wherein said immunogenic carrier material is bovine serum albumin.

3. The antigen of claim 1 wherein said $n$ is 2.

4. The antigen of claim 3 wherein the propranolol of said hapten is the l-enantiomer.

* * * * *